(12) United States Patent
Possover

(10) Patent No.: US 11,464,986 B2
(45) Date of Patent: Oct. 11, 2022

(54) DEVICE AND METHOD FOR NEUROMODULATION

(71) Applicant: Marc Possover, Hagendorn (CH)

(72) Inventor: Marc Possover, Hagendorn (CH)

( * ) Notice: Subject to any disclaimer, the term of this patent is extended or adjusted under 35 U.S.C. 154(b) by 486 days.

(21) Appl. No.: 16/523,136

(22) Filed: Jul. 26, 2019

(65) Prior Publication Data
US 2021/0023379 A1 Jan. 28, 2021

(51) Int. Cl.
*A61N 1/375* (2006.01)
*A61N 1/36* (2006.01)
*A61N 1/05* (2006.01)
*A61N 1/372* (2006.01)

(52) U.S. Cl.
CPC ....... *A61N 1/37512* (2017.08); *A61N 1/0521* (2013.01); *A61N 1/36007* (2013.01); *A61N 1/36107* (2013.01); *A61N 2001/37294* (2013.01)

(58) Field of Classification Search
CPC .............. A61N 1/37512; A61N 1/0521; A61N 1/36007; A61N 1/36107; A61N 1/0524; A61N 1/36017; A61N 2001/37294
See application file for complete search history.

(56) References Cited

U.S. PATENT DOCUMENTS

| | | | |
|---|---|---|---|
| 2003/0100930 A1* | 5/2003 | Cohen ................ | A61N 1/36007 607/40 |
| 2006/0004421 A1* | 1/2006 | Bennett .............. | A61N 1/36107 607/48 |
| 2010/0318098 A1* | 12/2010 | Lund .................... | A61N 1/0524 606/129 |
| 2011/0137114 A1* | 6/2011 | Schwartz ............... | A61K 31/47 600/38 |

* cited by examiner

*Primary Examiner* — Tammie K Marlen
(74) *Attorney, Agent, or Firm* — Bachman & LaPointe, P.C.

(57) ABSTRACT

The present invention relates to a preoperative test method, to an implantation system (20) and to an implantation method for implanting a neuroprosthesis in the area of the pubic bone (31), wherein implantation is ultimately simplified and made more effective directly or indirectly by the subject-matters of the invention.

18 Claims, 6 Drawing Sheets

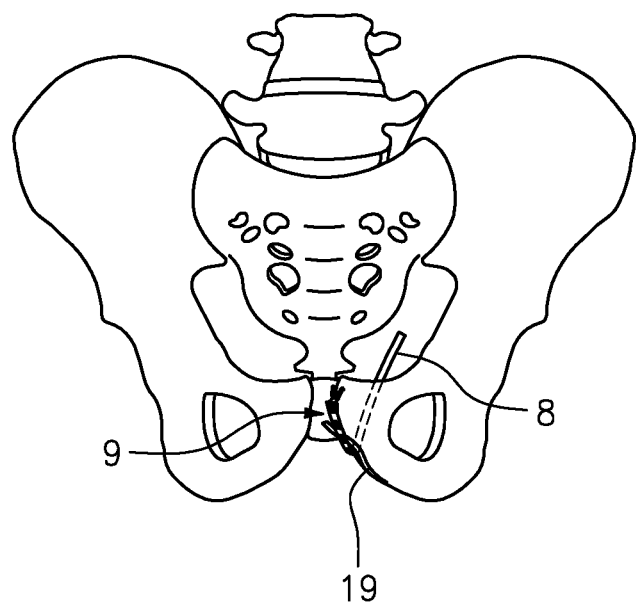
FIG. 9
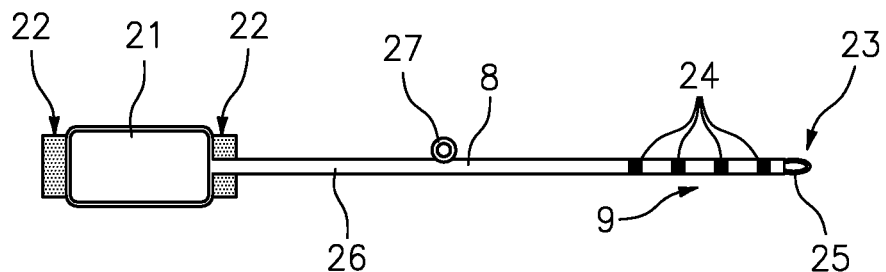
FIG. 10a
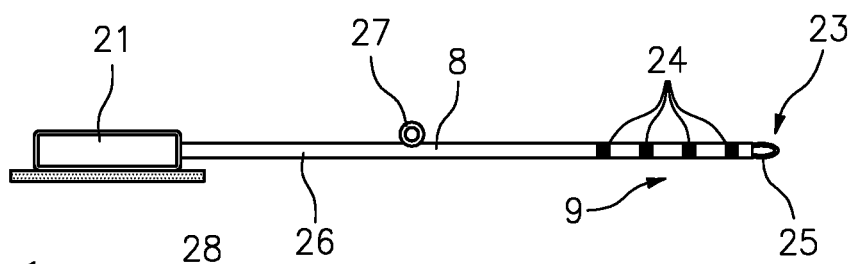
FIG. 10b
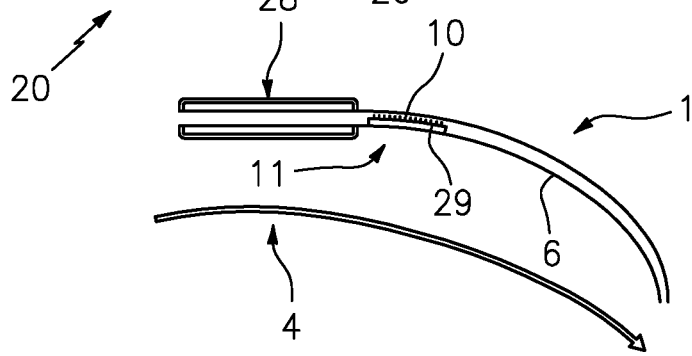
FIG. 10c
FIG. 10

DEVICE AND METHOD FOR NEUROMODULATION

BACKGROUND OF THE INVENTION

The present invention relates to devices and methods for neuromodulation. In particular, the present invention relates to a preoperative test method for implanting a neuroprosthesis for possible stimulation of nerves in the genital area, the neuroprosthesis comprising a pacemaker and an electrode array.

Over the past years, significant progress has been made in the field of neuromodulation or neurostimulation.

Various developments that relate to systems and devices employed in neuromodulation can be traced back to the applicant. Also, substantial progress in terms of the methods for introducing neuroprostheses into the human body that embody the endeavor of allowing the neuroprosthesis to be introduced into the body relatively easily, thus making it available to a maximum number of both patients and surgeons and minimizing the corresponding cost, can be traced back to the applicant.

Moreover, the applicant has made a multitude of findings relating to the use of neuroprostheses for stimulating nerves in the genital area. For instance, it has come to be known that neurostimulation of nerves in the genital area can alleviate and even cure different issues or disorders and can also be used as a preventive measure in order to prevent or at least greatly delay the development of a pathological condition of the body. The disorders or conditions that are to be or can be treated include fecal and/or urinary incontinence and erectile dysfunction. In preventive use, a neuroprosthesis for stimulating nerves in the genital area can be employed to prevent muscular atrophy, for example, which can occur in bedridden patients or when a person stays in a low-gravity environment for longer periods of time.

However, the progress achieved so far, which is documented in EP 2 389 975 B1, EP 2 767 306 A1, U.S. Pat. No. 10,232,175 B2 and U.S. patent application Ser. No. 16/228,991, for example, has different disadvantages that are in need of improvement.

For instance, according to the current state of the art, an implantation method for implanting a neuroprosthesis for stimulating nerves in the genital area as direct as possible involves two individual or two separate implantation steps because first a test array or a test neuroprosthesis is implanted, and if the nerves in the genital area are successfully stimulated, then a final or permanent neuroprosthesis is implanted. This approach leads to increased risks for the patient or the body to be treated because every implantation involves a certain risk. Additionally, the described approach is also expensive, which is why such a neuroprosthesis is available for only a certain percentage of bodies or patients for which the implantation is an option. Moreover, even as the methods for implantation of the neuroprosthesis have been continuously improved over the past, they still to some extent require specific skills or specialist knowledge of the implanting surgeon, which limits the total number or the circle of persons that are able to perform such an implantation of a neuroprosthesis or of a test neuroprosthesis.

Finally, a stimulation of the nerves as direct as possible is a significant factor for the success of the neurostimulation. In other words, this means that irrespective of whether a condition is to be treated or a healthy state is to be maintained or deterioration of a state of health is to be prevented, the results of the neurostimulation substantially depend on whether the wire electrode means which are comprised by the neuroprosthesis, in particular the contact portion or the contact ends of an electrode array which are comprised by wire electrode means and which are to transmit an electrical impulse to the nerve, can be placed in closest possible proximity to the nerve or nerve end and also permanently remain in that position after implantation. However, since the exact position or the exact path of the nerves may differ slightly from body to body, placement of the electrode array, in particular of the contact portion or of the contact end of the wire electrode means, as ideal and precise as possible and aligned to the anatomy of the respective body has to be ensured in order for the implantation of the neuroprosthesis, in particular of the electrode array remaining in the body for preferably a long time, to promise success. In this context, in particular during the implantation, resources or auxiliary methods such as imaging techniques can be used to only a very limited degree.

The nerves to be stimulated can be the dorsal nerve of the penis or of the clitoris. Other nerves, such as the perineal nerve, the parasympathetic nerve or the cavernous nerve, can be stimulated as well.

SUMMARY OF THE INVENTION

Against this background, the object of the present invention is to propose a preoperative test method for implantation of a neuroprosthesis comprising a pacemaker and an electrode array for stimulating nerves in the genital area as directly as possible by means of which information and data are obtained that form a basis for rendering implantation of a test array or of a test neuroprosthesis entirely dispensable and which additionally allows or at least facilitates individual positioning as precise as possible of the electrode array, in particular of the contact portion of a wire electrode array, in the area of the nerves.

Another object of the present invention is an implantation system whose devices allow the electrode array to be positioned particularly well or effectively, allowing the nerves to be stimulated as directly as possible by the contact end or the contact ends of the array with the neuroprosthesis.

Finally, the object of the present invention is to enhance an implantation method, the enhanced method constituting a significant simplification compared to known methods and at the same time allowing the contact portion or the contact end of the wire electrode means comprising the electrode array to be positioned ideally and/or as reliably as possible in the area or in the immediate proximity to the nerves to be stimulated.

With regard to the preoperative test method for implanting a neuroprosthesis comprising a pacemaker and an electrode array for stimulating nerves in the genital area as directly as possible, the object is attained with the following method steps:

placing removable, preferably adhesive electrodes on the body surface of a genital area of the patient or of the body to be treated; inducing in the patient or the body to be treated a physical condition that exhibits the symptoms to be treated with the neuroprosthesis; energizing the electrodes with a test current; recording the change caused in the symptoms by the energization of the electrodes with a test current.

The basic idea behind the test method according to the invention or the surprising finding that the preoperative test method is based on is the fact that even an electrode array that is placed on the body surface, i.e. without invasive surgery, and its energization can be used to achieve indirect stimulation of the nerves in the genital area that have a certain correlation with the physical condition to be treated.

Since part of the genital nerves (dorsal nerve and cavernous nerve) is located superficially below the skin outside of the pelvis and not within the genital organs themselves, these nerves can be stimulated using surface electrodes attached to the overlying skin of the penis or in proximity to the clitoris. By recording the change in the symptoms of the physical condition to be treated in conjunction with or after energization of the electrodes placed in the genital area, the data-related basis can be established in order to make a decision based thereon whether and in which form an implantation of a final neurostimulator or of a neuroprosthesis for long-term use in the body seems sensible and expedient without subjecting the patient or the body to be treated to the risk of an operation or surgery.

In other words, this means that from the preoperative test method and from the data obtained through it, in particular in the form of the records of the change in the symptoms of the physical condition to be treated, information can be obtained or becomes accessible that, in turn, allows or facilitates a decision as to whether the physical condition to be treated can be successfully treated by permanent implantation of a neuroprosthesis.

A particular advantage of the preoperative test method according to the present invention aside from the avoidance of any surgical or operative interventions on the body or in the body is that the test method can be performed by anyone with little or negligible instruction. This means that the preoperative test method does not have to be performed by medically trained personnel or under the supervision of medical personnel. Instead, the test method can be performed by the person to be treated, for example, and particularly preferably in their home environment. This has the advantageous effect that the costs for performing the method are significantly reduced. Moreover, the individual's sense of modesty, which tends to vary greatly between cultures, is also considered, which is why, psychologically or psychosocially, the proposed test method will be met with significantly more acceptance than, for example, a test method in which medical personnel or at least paramedical personnel has to be present or even has to perform individual steps of the test method on the body to be treated.

When recording the change caused in the symptoms by the energization of the electrodes, very different options for documentation or recording can be employed. On the one hand, the change or, as the case may be, the absence of change can be documented by hand, preferably by answering a ready-made questionnaire. However, other options can be used as well. For instance, a test device employed to perform the method can comprise an input interface or an input device through which the change in the symptoms as perceived by the person performing the test method are entered and thus documented Finally, additional sensors or sensor devices which allow a largely objective recording of the changes in symptoms can be used. The treatment or therapy of erectile dysfunction is used as an example: The test method could be performed while the test subject or the test body is subjected to sexual stimulation. The change caused in the symptoms by the energization of the electrodes could be recorded by measuring and recording the blood flow into the cavernous bodies of the penis by means of suitable sensors. Furthermore, a mechanical measurement registering and recording the mechanical changes in the tissue of the penis and thus the occurrence or absence of an erection could be used to record the change in symptoms. According to a first advantageous variation of the method, the electrodes may be energized with a test current with current pulses of 150 µs to 250 µs in length and preferably a frequency of 10 Hz to 50 Hz, particularly preferably with an amplitude of 5 mA to 60 mA. Current pulses in this range have proven particularly suitable for registering or making registerable a change in the symptoms of the physical condition to be treated without subjecting the body to be treated to pain or causing pain. Moreover, such test current pulses are preferred because pulse generators that can generate such pulses are known from other medical fields and electrodes, in particular removable adhesive electrodes that can couple or transmit current pulses of this kind into the body via the skin of the body to be treated.

According to another preferred variation of the test method, a first electrode may be placed in the area of the clitoris or of the root of the penis and a second electrode may be placed at the same height at a lateral offset of two to three centimeters (2 to 3 cm) from an outer labium or at a lateral offset of two to three centimeters (2 to 3 cm) from the root of the penis. This electrode array has proven particularly effective in generating an indirect stimulation of the nerves in the genital area from outside and thus in making the change in a physical condition exhibiting the symptoms to be treated visible or registerable.

According to another advantageous variation of the test method, laterally offset placement of the second electrode may be performed successively on both sides of the body, and upon each placement, at least the method steps of inducing a physical condition exhibiting the symptoms to be treated with the neuroprosthesis, energizing the electrodes with a test current and recording the change caused in the symptoms by the energization of the electrodes are executed. It was very surprisingly found that the placement of the laterally offset electrode on different sides of the body and the corresponding recording of the change caused in the symptoms by the energization of the electrodes leads to valuable and interesting data being recorded, which adds significantly to the data basis generated with the test method overall and facilitates evaluation of the data or the unambiguousness of a potential evaluation of the data.

According to another advantageous variation of the method, each laterally offset placement of the electrode is performed at a different height with respect to the first electrode, and upon each placement, at least the method steps of inducing a physical condition exhibiting the symptoms to be treated with the neuroprosthesis, energizing the electrodes with a test current and recording the change caused in the symptoms by the energization of the electrodes are executed. A range of 0.5 to 2 centimeters, preferably 0.5 to 1.5 centimeters, has proven advantageous as a possible variation of the height of the second electrode with respect to the placement of the first electrode. Like in the case of the respective testing of both sides or halves of the body, the variation in height of the second electrode relative to the first electrode can compensate or reflect slight personal or individual anatomical differences, the record or data on the physical reaction to the energization of the electrodes obtained with the test method offering a valuable basis for avoiding test implantation of a neuroprosthesis and instead being able to directly access a final implantation of a neuroprosthesis based on the records obtained and subsequently perform it, if applicable.

According to another particularly preferred variation of the test method, the second electrode is configured and used as a multiple electrode comprising a plurality of spatially adjacent and electrically separate and individually controllable individual electrodes, the method being performed in such a manner that the different electrodes are energized in a temporal order. Here, too, a record is generated for the energization of each of the different individual electrodes of the multiple electrode, the records documenting the change caused in the symptoms of the physical condition by the energization of the electrodes.

The use of a multiple electrode with multiple individual electrodes has the advantage that the position of the second electrode can be changed without having to reposition the electrode itself. This has the advantage that since the second electrode is not repositioned, the disadvantageous effects accompanying repositioning, such as a decrease in adhesion of the adhesive electrode on the skin and/or a decreasingly effective coupling-in of the test current into the body due to a decrease in conductivity, are absent. Moreover, defined relative spatial positions are established with an electrode having a plurality of individual electrodes because the electrodes have a fixed spatial relationship to one another. If the initial or single positioning of the second electrode can also be performed with a certain reliability or precision, the fixed relative positions of the individual electrodes relative to one another can also provide valuable information in connection with the records on the physical reactions to the test current or the energization of the individual electrodes, said information having proven particularly valuable with a view to an implantation of a neuroprosthesis.

According to another preferred variation of the method, the first electrode may be energized as a cathode and the second electrode may be energized as an anode, polarity preferably reversing during energization and the change caused in the symptoms by energization being recorded as a function of the polarity of the electrodes. A change in the symptoms as a function of the current direction or as a function of the polarity of the electrodes can, in connection with the recording, provide important information on the usefulness and the exact execution of an implantation of a neuroprosthesis for stimulation, in particular for the most direct stimulation possible, of nerves in the genital area.

According to another particularly preferred variation of the method, the condition to be treated comprises urinary incontinence, fecal incontinence and/or erectile dysfunction. Also, irritable bladder, overactive bladder (neurogenic, non-neurogenic, idiopathic), detrusor sphincter dyssynergia and/or erectile dysfunction, libido disorder and/or ejaculatory disorder in men or orgasmic, clitoral or libido disorders in women may be the condition to be treated. Advantageously, however, other physical conditions may be treated or the occurrence of certain conditions may be prevented, as well. Furthermore, other physical conditions may be treated, such as conditions involving disturbed signal transmission of the neural pathways in the spine.

Furthermore, the condition can be one of the following: restoration of the pelvic organs and pelvic floor muscle functions in neurogenic disorders such as spina bifida, multiple sclerosis, dementia or spinal cord injuries; control/improvement of the function of the genital organs including hormonal function (ovulation, hormone production of the ovaries). Other applications may include treatment or prevention of pathologies of the genital organs, such as endometriosis, adenomyosis or even deep infiltrating endometriosis of the rectovaginal space, myomas, functional uterine malfunctions; control of certain psychological and other conditions of the autonomous nervous system, such as neurogenic and idiopathic depression and psychosis/neurosis; control/improvement of function of the genital organs including hormonal function (ovulation, hormone production of the ovaries); management of neuropathic genitoanal, pudendal, urethral and vesical chronic pain (vulvodynia, coccydynia, pudendal pain, sacral radiculopathy, . . . ). The dorsal nerve of the penis is composed of different axon populations for stimulating the penis shaft, the urethra and the glands and, in women, for stimulating the urethra, the vulva and the clitoris.

When the neuroprosthesis is used preventively, the method step of producing a physical condition can be omitted; instead, energization can be performed and the physical reactions can be subjectively and/or objectively recorded and/or measured. The reason for this is that when a neuroprosthesis is used preventively, there is no prevailing condition to alleviate or treat. Instead, the development of such a condition is to be counteracted. To this end, it may be sufficient to record whether any physical reactions to an energization of the electrodes can be detected and what they are.

The object stated above is also attained by an implantation system comprising a curved hollow needle applicator which can accommodate a tip in a shaft surrounding a hollow needle channel, the tip preferably being comprised by the system and removable at the front end, or can accommodate a wire electrode means at the front end, the wire electrode means being comprised by the system, wherein, according to the invention, the hollow needle applicator comprises a measuring device by means of which a user can determine how far the wire electrode means has been introduced into the shaft of the hollow needle applicator at the front end.

As described above in connection with the preoperative test method, the object of the present invention is to provide methods and devices that achieve an even better stimulation as direct as possible of nerves in the genital area by means of a pacemaker and an electrode array connected to the pacemaker and in particular comprising a wire electrode means. The test method serves to obtain information that is suitable for determining whether an implantation of such a neuroprosthesis seems sensible; furthermore, the method can also serve to be able to better specify how and where the electrode array, in particular the contact portion of a wire electrode means of an electrode array, has to be positioned in order to allow a stimulation of the nerves in the genital area that is as direct and thus as effective as possible. However, in order to not only make the knowledge of an ideal implantation site of the electrodes, in particular of the contact ends of the wire electrode means, determinable, but also to additionally ideally adapt the implantation method to the derivable information, it has proven particularly advantageous for a generic hollow needle applicator to be configured in such a manner that the measuring device allows the surgeon to see how far the wire electrode means is currently introduced into the hollow needle applicator during implantation so as to be able to conclude therefrom whether said length or the length of the wire electrode means available for implantation is sufficient or properly adjusted in order to achieve ideal positioning of the contact portion of the wire electrode means in the area of the genital nerves.

As will be explained in more detail below, this is because it is of significant importance in the implantation method that the contact portion of electrode array or of the wire electrode means is/are placed as closely as possible to or at the smallest possible spatial distance from the nerves to be stimulated and remain(s) there permanently. To this end, however, it is of significant importance for the length of the wire electrode means to be selected correctly or set correctly even if the implantation method is performed with the help of imaging technology. This also applies in particular because it is especially important for long-term treatment or effective prevention of physical conditions that the wire electrode means and especially the contact ends remain at the implantation site after implantation because only then permanent effective stimulation of the nerves can be ensured.

Accordingly, it has surprisingly proven highly effective for the hollow needle applicator to be equipped with a measuring device via which the user can determine how far a wire electrode means has been introduced into the shaft of the hollow needle applicator at the front end.

The measuring device can basically be configured in different ways. For instance, in a first advantageous configuration, the measuring device can be realized in the form of a window in the area of the shaft of the hollow needle applicator, the window being provided with a scale and/or a mark so that the user can optically determine through the window and with the aid of the scale whether and how far a wire electrode means has been introduced into the shaft. The scale and/or the mark can also be configured for interaction with the window. In any event, the scale, the mark or the measuring device in general may be settable or adjustable in order to, for example, be able to adjust them to the results of an evaluation of the records of the test method and to thus individualize the system and/or the hollow needle applicator for each patient or each body.

However, other, significantly more complex devices can be used to realize the measuring device. For example, the measuring device can be configured in such a manner that a change in the electrostatic properties of the hollow needle applicator caused by the introduction of the wire electrode means is detected and converted into a corresponding measuring signal. Alternatively or additionally, a magnetic measuring method can form the basis of the measuring device, in which case the magnetic properties of the hollow needle applicator or of the combination of the hollow needle applicator and the wire electrode means are preferably also measured, and the position or the introduction depth of the wire electrode means are determined or measured therefrom. Here, too, individualization and/or adjustment to the respective body can be envisaged, preferably taking into account the information of the test method.

In particular in order to ensure permanent function or effect of the neurostimulation after successful implantation of a neuroprosthesis comprising wire electrode means or electrode arrays, it is important, as indicated above, that the wire electrode means, in particular the contact portion of the wire 25 electrode means, remain at the implantation site and will not be repositioned or shifted by body movements or other influences, for example. To this end, in a preferred embodiment, the system according to the invention comprises a fixing means on the contact portion of the wire electrode means by means of which the wire electrode means can be fixed to a cartilage and/or bone structure, preferably to the pubic bone. This not only allows ideal implantation of the wire electrode means in particular in connection with the measuring device of the hollow needle applicator, but also ensures that specifically the contact portion of the contact portion of the wire electrode means that includes the electrodes permanently remains in an advantageous position that enables the effect of the neuroprosthesis.

According to another advantageous embodiment, the wire electrode means of the system may have a mobile fixing means in a shaft area, which is preferably disposed between a contact portion and a connecting portion to the pacemaker, the mobile fixing means allowing the wire electrode means to be fixed to a cartilage and/or bone structure, preferably to the pubic bone, the mobile fixing means preferably being configured in such a manner that it allows movement relative to the hollow needle applicator.

Moreover, with such a mobile fixing means, a fixation of the wire electrode means that is particularly ideal and adjusted to the anatomical conditions can be established, preferably in the area of or on the pubic bone; to this end, the fixing means is preferably moved onto or positioned on the shaft portion of the wire electrode means in such a manner that the fixing means is placed in a portion of the wire electrode means that will be placed as close as possible to the cartilage and/or bone structure, preferably the pubic bone, when neuroprosthesis, and thus a wire electrode means, has been implanted. After fixation between the wire electrode means and the cartilage or bone structure has been established via the mobile fixing means, the mobile fixing means may also be fixed to the wire electrode or to the wire electrode means. Alternatively, however, it may also be advantageous if the mobile fixing means is fixed to the cartilage or bone structure only and mobility relative to the wire electrode means is maintained on the whole or at least to a limited degree so as to preserve some flexibility or to provide some compensability.

Furthermore, the object of the invention is attained by an implantation method for a wire electrode means in the pelvic area of a body, the method comprising the following steps:

producing a first temporary implantation channel running from the genital area behind the pubic bone to the abdominal wall for receiving the wire electrode means; introducing the wire electrode means into the first implantation channel from the abdominal wall in such a manner that a contact portion of the wire electrode means protrudes from the body, in particular from the first implantation channel, in the genital area;

producing a second temporary implantation channel which ventrally or in front of the pubic bone in the genital area, in particular in the area of the pelvic floor, and whose exit area from the body coincides with an entry area of the first implantation channel located in the genital area, the contact portion of the wire electrode means thus being introducible into the second implantation channel, transferring the contact portion of the wire electrode means protruding from the body into the second implantation channel in such a manner that electrodes disposed in the contact portion, in particular circumferential electrode means, are placed in the area of the roots of the nerves in the genital area.

The proposed implantation method is characterized in particular by the fact that compared to known methods, it is relatively simple and safe to perform, which is why it can be performed by a large number of users or surgeons.

Moreover, as will be explained in more detail below, particularly reliable positioning of the contact portion of the wire electrode means in direct proximity to the nerves to be stimulated can be achieved with the method according to the invention. As will also be explained in more detail later, the method additionally allows the risk of later shift or delocalization of the wire electrode means, in particular of the contact portion, to be prevented or at least the danger thereof to be significantly reduced compared to known implantation methods by guiding of the wire electrode means.

According to an advantageous embodiment of the implantation method, the wire electrode means may be anchored to a cartilage and/or bone structure, preferably to the pubic bone. In this way, an unintentional shift or repositioning of the wire electrode means implanted with the implantation method is prevented or minimized.

Particularly preferably, the wire electrode means may have a fixing means on a contact portion including the electrodes, the fixing means being used to fix the wire electrode means to a cartilage and/or bone structure, preferably to the pubic bone.

In this way, the part of the wire electrode means on which the electrodes or the contact ends are disposed and via which the nerve(s) is/are stimulated is fixed in a particularly advantageous manner.

Additionally or alternatively, according to an advantageous variation of the method, the wire electrode means may also have a mobile fixing means in a shaft portion that is preferably disposed between a contact portion and a connecting portion for being connected to a pacemaker, the wire electrode means being fixed to a cartilage and/or bone structure, preferably to the pubic bone, via the mobile fixing means in the course of the method. In this way, preferred fixation of the wire electrode means can further be achieved, shifting or slipping of the wire electrode means after implantation of the neuroprosthesis being prevented.

In another particularly preferred embodiment of the implantation method, the first and/or the second implantation channel may be produced using a curved hollow needle applicator which comprises a hollow needle channel enclosed by the shaft and forming the respective implantation channel. Thereby, it can be insured that the electrode comprising the electrode wire means is laid or moved along a defined implantation channel, wherein, particularly preferably, not only does the hollow needle applicator serve to produce the respective implantation channel, but the hollow needle channel enclosed by the shaft of the hollow needle applicator also allows the electrode wire means to be accommodated and to be implanted or laid without any potentially disadvantageous further interaction with the surrounding tissue.

Particularly preferably, during production of the first and/or the second implantation channel, a tip removable from the hollow needle applicator at, preferably, the front end, closing the access to the hollow needle channel and preferably partially filling the hollow needle channel is placed on the hollow needle applicator. This has the advantage that unintentional damage to or unnecessary interference with the surrounding tissue is prevented while the necessary penetration of specific tissue layers or tissue areas is facilitated.

Furthermore, the tip has the advantage that, in particular during production of the implantation channel or channels, the hollow needle channel is closed and thus no objects, such as tissue or fluids, can enter the hollow needle channel. This, in turn, facilitates introduction of the wire electrode means into the hollow needle channel for laying or implanting the wire electrode means because the wire electrode means can be easily introduced into the hollow needle channel.

According to a particularly preferred embodiment, the tip may be removed from the hollow needle applicator extracorporeally, preferably at the front end, after the respective implantation channel has been produced. This leads to the significant facilitation that without a corresponding spatial constriction or narrowing, the tip can be removed from the hollow needle applicator by hand or using a suitable tool. Moreover, this approach allows optical inspection of the hollow needle applicator and of the corresponding hollow needle channel at least in the area of the front end of the hollow needle applicator.

According to a particularly preferred variation of the method, in order to produce the first implantation channel, a curved hollow needle applicator, while being in contact with the lower edge of the pubic ramus, is introduced until it penetrates the urogenital diaphragm, the retropubic space and the abdominal wall, exit from the abdominal wall preferably being performed in such a manner that the exit occurs above the pubic bone and, particularly preferably, a shaft of the hollow needle applicator surrounding the hollow needle channel is in contact with the pubic bone. This approach makes producing the first implantation channel particularly simple for the user or surgeon.

Also, after production of the respective implantation channel and respective introduction of the wire electrode means into the hollow needle channel, the hollow needle applicator may be removed from the body, preferably by retracting the hollow needle applicator in the direction of a puncture or in the direction of an entry point of the hollow needle applicator during production of the respective implantation channel. This allows the hollow needle applicator, in particular the hollow needle channel, to ensure ideal guiding of the wire electrode means after production and during maintenance of the respective implantation channel, simple and risk-free removal of the hollow needle applicator being possible once the wire electrode means has been positioned, whereby the implantation channel is voided and collapses.

Likewise, according to an advantageous variation of the method, producing the first implantation channel may comprise making an incision, the incision being made in the genital area of the body, in particular 0.5 cm to 1.5 cm below the external urethral meatus or 0.5 cm to 1.5 cm below the infrapubic parapenile. At this site, incisions or punctures are possible relatively easily and without excessive risk and additionally allow an overall advantageous procedure.

Moreover, producing the second implantation channel may advantageously comprise making a second incision and/or puncture, the second incision and/or puncture, in particular on a median axis of the body, being made below the caudal border of the inferior pubic ramus, especially preferably just above the root of the penis or of the clitoral glands and laterally offset therefrom by 3 mm to 5 mm. In this area, too, such a puncture or incision can be easily made with relatively little risk. Moreover, together with the previously described advantageous first puncture or incision, this puncture or incision allows particularly advantageous guiding of the wire electrode means in the body because it may thus be ensured that starting from the pacemaker, the wire electrode means coming from a rearward area is guided below the pubic bone and around the pubic bone in such a manner that a most direct stimulation possible of the nerves in the genital area is possible after implantation and that belated shifting or slipping of the wire electrode means, in particular of the contact portion or of the contact ends, is avoided to the largest possible extent or precluded.

According to another preferred variation of the method, a connecting end of the wire electrode means that faces away from the contact portion may be connected to a pacemaker which is placed behind the pubic bone, preferably opposite the contact portion of the wire electrode means. This allows simple and reliable placement of the pacemaker. At the same time, a simple and reliable contact or connection between the pacemaker and the wire electrode means is achieved. The corresponding placement of the pacemaker behind the pubic bone plays a large part in making a particularly preferred guiding of the wire electrode means possible, in which the wire electrode means is guided from the pacemaker to behind the pubic bone to under the pubic bone and around the pubic bone, whereby guiding of the wire electrode means and placement of the wire electrode means in a way that makes it highly unlikely that the wire electrode means will shift or move after implantation, which would affect or prevent successful and effective stimulation of the nerves in the genital area, is made possible on the whole.

Likewise, according to a particularly preferred variation of the method, the surgical method steps may be performed under general anesthesia, spinal anesthesia or epidural anesthesia. This is a particularly advantageous variation because for testing the success of the implantation of the neuroprosthesis, in particular of the electrodes of the wire electrode means, the known methods so far had to make sure that the patient or the body to be treated verified or assessed the successful positioning of the electrodes and thus the possible stimulation of the genital nerves by themselves. This, in turn, meant that the implantation method could not be performed under general anesthesia, spinal anesthesia or epidural anesthesia because these types of anesthesia did not allow interaction with or feedback from the patient or the body to be treated that would permit assessment or determination of a successful implantation or placement of the wire electrode means, in particular of their electrodes. However, owing to the improved procedure, ideal orientation of the wire electrode means and in particular of the electrodes in the contact portion is achieved overall with very high likelihood using the proposed method, which means that types of anesthesia can preferably also be used in which communication with the patient, in particular any sort of sensation of the patient, is impossible and/or unnecessary. However, the method according to the invention can also be performed under local anesthesia, such as IV sedation. Also, success of the implantation can be checked, for which purpose the electrode is energized and the patient, who is only locally anesthetized, gives feedback on his/her sensations. Therefore, no neurophysiological measurement has to be performed. In case the test phase has not been conclusive, there is always the possibility to implant an electrode according with the reported technique, to repeat a test phase using an external pacemaker, with in case of success a secondary implantation of the pacemaker under local anesthesia.

Likewise, according to a particularly preferred variation of the method, the implantation method may comprise a preoperative test method according to any one of claims 1 to 9. This circumvents implantation of a test neuroprosthesis, on the one hand. On the other hand, the method, in particular the surgical procedure, can be performed in a manner ideally adjusted to the individual if conclusions as to the ideal position of the wire electrode means, in particular of the contact portion comprising the electrodes, are drawn from the information recorded and obtained via the energization with the test current.

In this context, but not limited to the correlation with the implantation method, it should be noted that the information obtained in the course of the preoperative test method by recording the change in the symptoms of the physical condition to be treated may advantageously be used to assess a therapeutic outcome that can be expected after implantation of a neuroprosthesis and/or to assess an ideal performance of an implantation method and/or an ideal implantation site for an electrode array, in particular of a contact portion including electrodes or of a contact end of a wire electrode means. This means that the records of the preoperative test method are used—automatically, if applicable, based on predefined criteria and rules, for example, or intellectually—to make an assessment by way of evaluation with which the therapeutic outcome to be expected overall and, moreover, an ideal procedure during performance of a method for implantation of a neuroprosthesis can be measured and/or determined.

BRIEF DESCRIPTION OF THE DRAWINGS

Hereinafter, the invention will be illustrated based on schematic drawings.

FIGS. 1 to 9 illustrate different method steps for performing the implantation method for a wire electrode means of a neuroprosthesis;

FIGS. 10*a* to 10*c* are schematic illustrations showing an implantation system according to the invention; is an exemplary illustration in connection with a performance of the preoperative test method for an implantation of a neuroprosthesis.

DETAILED DESCRIPTION

Figure 1:
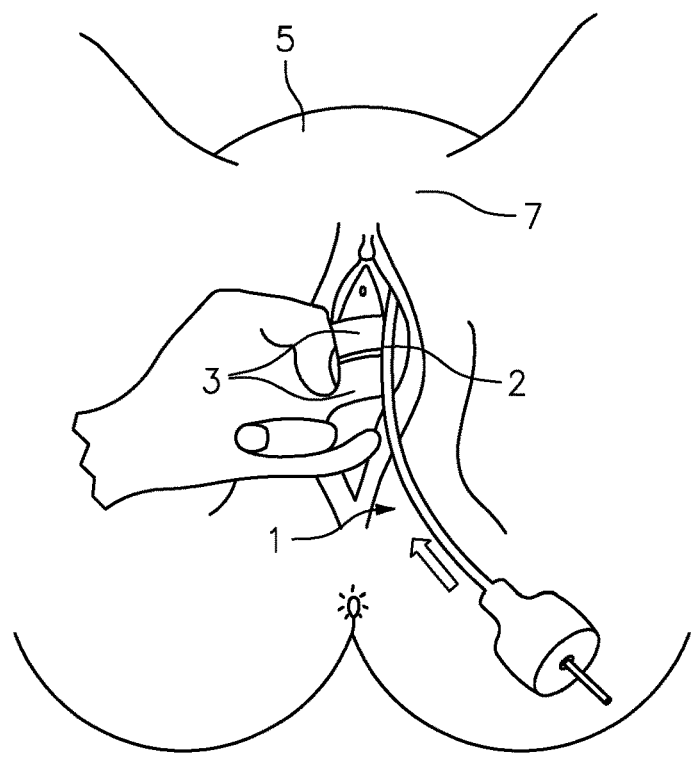

FIG. 1 shows a first method step for performing the implantation method. The exemplary illustration of the implantation method is described with reference to the body of a human female. However, the implantation method according to the invention can also be performed on male bodies and on bodies of mammals having an anatomy similar to that of the human body. In the first method step of FIG. 1, a paravulvar incision 2 or first incision 2 is made, which allows a hollow needle applicator 1 to be introduced into paravulvar incision 2. Alternatively, a first puncture can be made. The incision and path of hollow needle applicator 1 are selected such that hollow needle applicator 1 is introduced behind and in direct contact with the dorsal part of the pubic bone, the path of hollow needle applicator 1 preferably being controlled and/or monitored with two fingers 3 inserted into the vagina. Hollow needle applicator 1 is not directed at the center (lesion of the urethra), but at an angle to the center so as to be able to exit between the median plane of the body and the groin area on the same side of the body as the vulvar incision. In the process, abdominal wall 5 behind the pubic bone is transfixed by hollow needle applicator 1.

Paravulvar incision 2 or first incision 2, which serves to produce a first implantation channel 7, is preferably made 0.5 cm to 1.5 cm below the external urethral meatus or 0.5 cm to 1.5 cm below the infrapubic parapenile.

Figure 2:
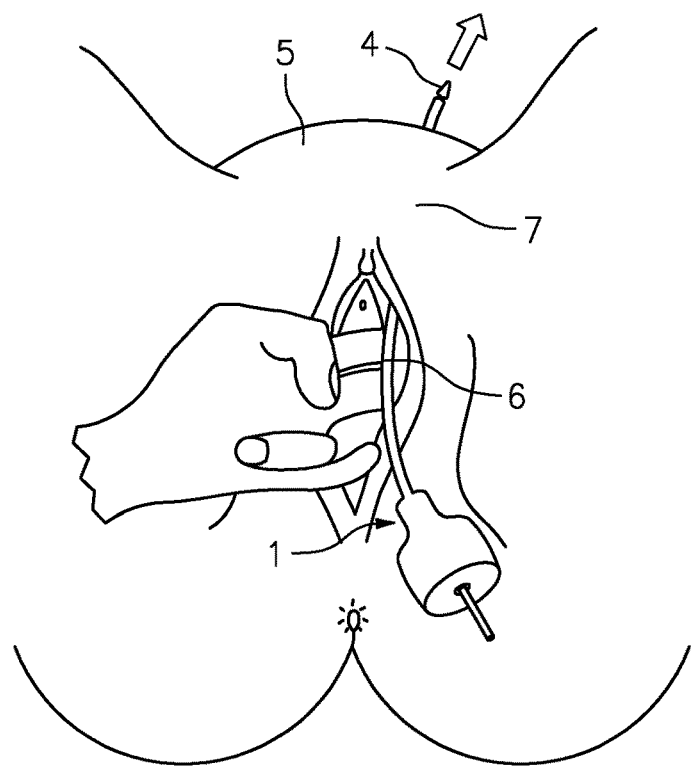

In the illustration of FIG. 2, the situation after completion of a first method step and during performance of a second method step is shown. Hollow needle applicator 1 including a tip 4 removable at the front end has emerged from abdominal wall 5, for which purpose curved hollow needle applicator 1 is guided while being in contact with the lower edge of the pubic ramus until it penetrates the urogenital diaphragm and the retropubic space and reaches the abdominal wall, the exit from abdominal wall 5 preferably being performed in such a manner that the exit happens above the pubic bone and a shaft 6 enclosing a hollow needle channel of hollow needle applicator 1 preferably is in partial contact with the pubic bone. The directional arrow in the illustration of FIG. 2 additionally indicates the retrograde removal of tip 4, which is removable from hollow needle applicator 1 and blocks access to the hollow needle channel, shaft 6 of hollow needle applicator 1, which surrounds the hollow needle channel, forming a first implantation channel 7 after removal of tip 4.

Figure 3:
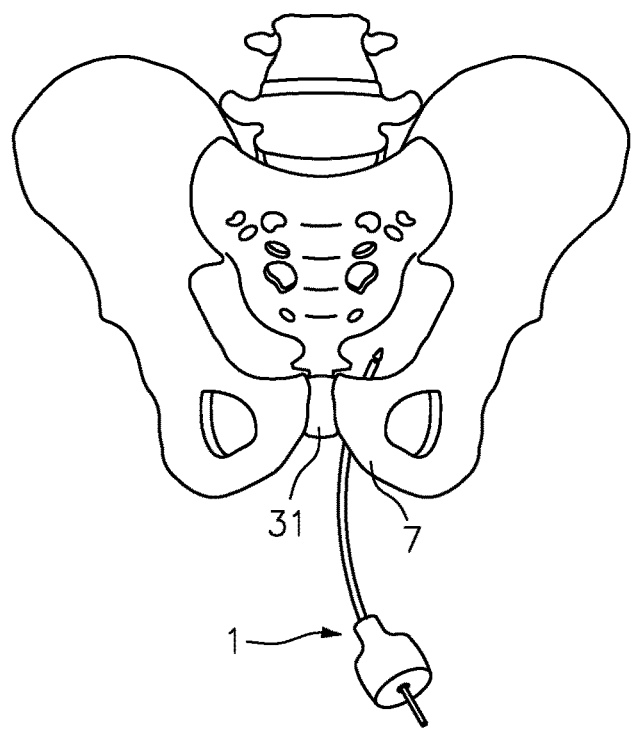

FIG. 3 illustrates once more the path of hollow needle applicator 1 during production of first implantation channel 7, for which purpose hollow needle applicator 1 is moved from behind pubic bone 31 through the avascular retropubic space.

Figure 4:
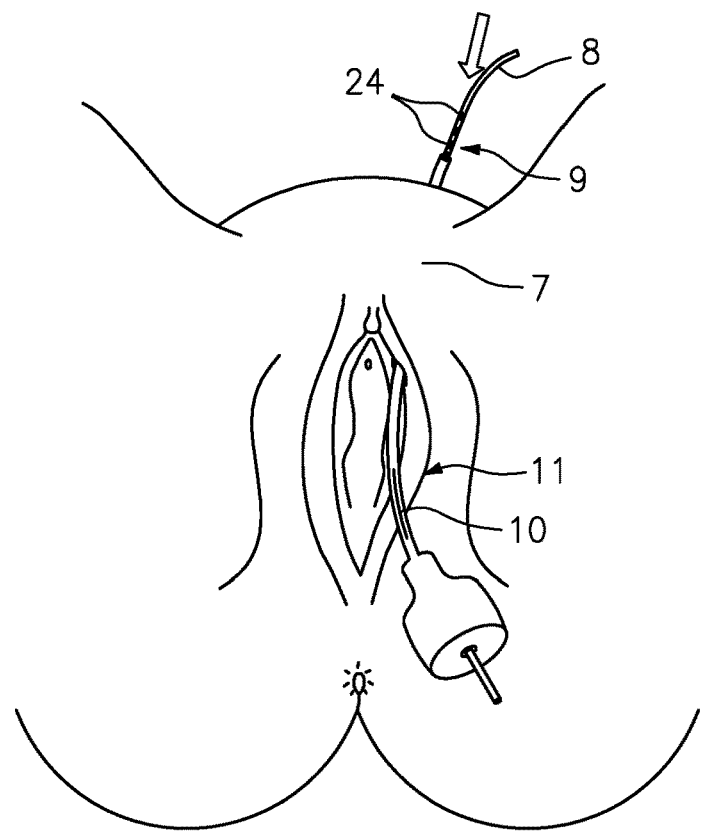

FIG. 4 illustrates a subsequent method step in which a wire electrode means 8 is introduced with a contact portion 9 first into first implantation channel 7, which is formed by the hollow needle channel of hollow needle applicator 1 and limited by shaft 6 of hollow needle applicator 1. This means that after removal of tip 4 from the front end or retrograde end of hollow needle applicator 1, wire electrode means 8 is also retrogradely introduced into hollow needle applicator 1 starting with the end that comprises electrodes 24 or the contact portion. To ensure that wire electrode means 8 are introduced far enough, but not too far into the first implantation channel, the shaft of hollow needle applicator 1 has a window 10 having a scale or mark (not shown), window 10 together with the mark and/or scale serving as a measuring device 11 with which the user can determine how far wire electrode means 8 has been introduced into shaft 6 of hollow needle applicator 1 at the front end or retrograde end.

After introduction of wire electrode means 8 into shaft 6 of hollow needle applicator 1 and thus into first implantation channel 7, a sufficiently far, but not too far introduction being preferably ensured via measuring device 11 of hollow needle applicator 1 during introduction of wire electrode means 8, hollow needle applicator 1 is removed from the body in a method step not shown, hollow needle applicator 1 being removed by retraction of hollow needle applicator 1 in the direction of incision 2 or in the direction of the point of entry of hollow needle applicator 1.

Figure 5:
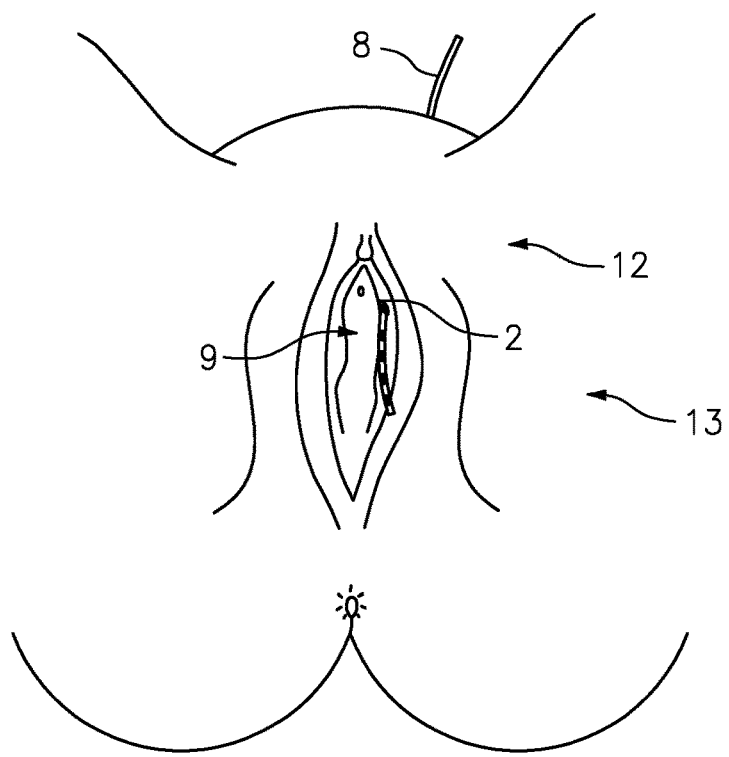

This results in a situation as schematically illustrated in FIG. 5. After removal of hollow needle applicator 1, wire electrode means 8 is accommodated in first implantation channel 7 from the direction of the abdominal wall in such a way that a contact portion 9 of wire electrode means 8 protrudes from body 13 in genital area 12, the contact portion of wire electrode means 8 protruding from the first incision or paravulvar incision 2.

Figure 6:
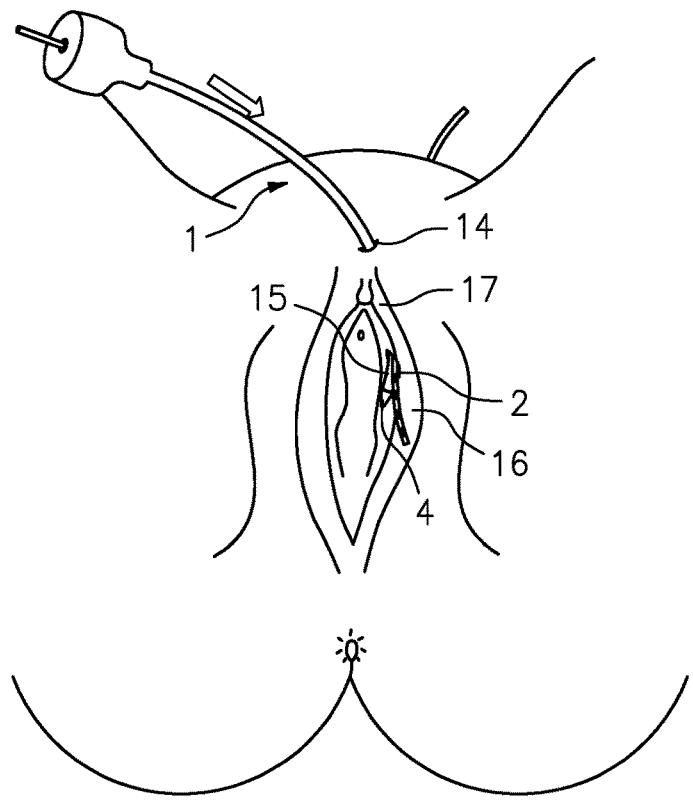

Another method step is outlined in FIG. 6. In the course of the next method step, hollow needle applicator 1 with reinserted tip 4 is introduced from the top to the bottom as deeply as possible through a second median supravulvar incision or second incision 14 and exits again through first incision 2 or paravulvar incision 2. Hollow needle applicator 1 is guided ventral of the pubic bone, but as closely as possible along the pubic bone so as to ensure that wire electrode means 8, in particular contact portion 9, is placed as deeply within the body as possible. The reintroduction of hollow needle applicator 1, starting from second incision 14 and exiting from first incision 2 as illustrated in FIG. 6, produces a second temporary implantation channel in the genital area, in particular in the area of the pelvic floor below the pubic bone, whose exit area from body 13 coincides with an entry area 16 of first implantation channel 7 in genital area 12. In this way, second implantation channel 17 is produced between second incision 14 and first incision 2 via shaft 6 of hollow needle applicator 1.

Figure 7:
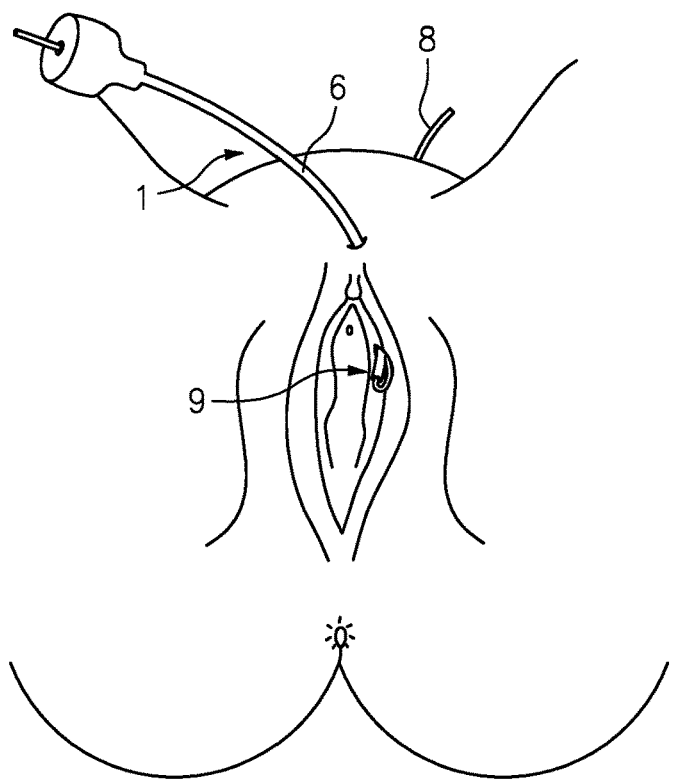

Following the production of second implantation channel 17, removable tip 4 is again removed from hollow needle applicator 1 at the retrograde end or front end. After removal of tip 4, wire electrode means 8 is introduced into shaft 6 of hollow needle applicator 1 from the retrograde end or front end with contact portion 9 first, shaft 6 again providing and maintaining the second implantation channel, as outlined in FIG. 7.

Figure 8:
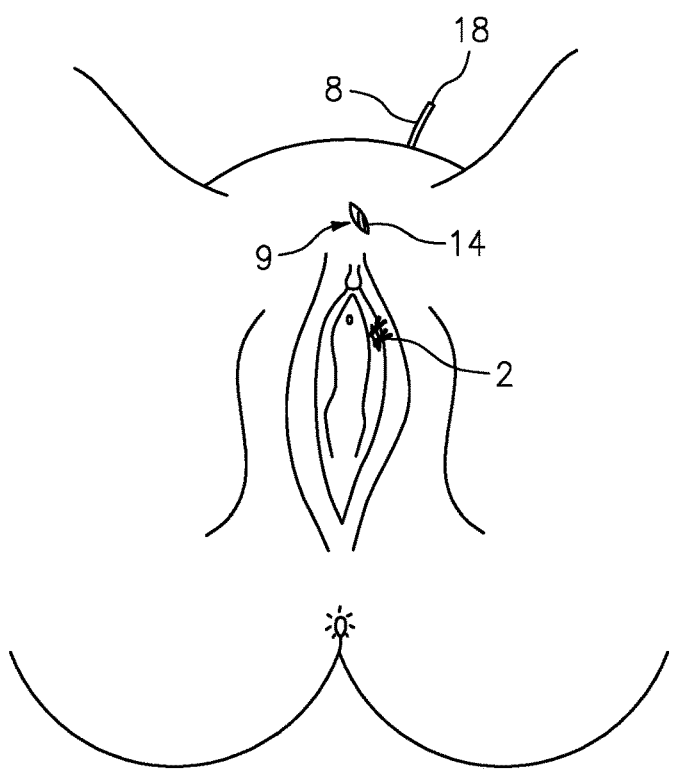

FIG. 8 shows a subsequent state of the implantation method, in which, after removal of hollow needle applicator 1, the wire electrode means, in particular contact portion 9, have reached their final position. Preferably, a fixing means provided in contact portion 9 may be used to fix the wire electrode means to, for example, the pubic bone by means of non-absorbable suture material in order to prevent migration of wire electrode means 8, in particular of contact portion 9. Also, both incisions 2 and 14 are closed, for which absorbable suture material can preferably be used. In another method step (not shown), a pacemaker is fixed or installed behind the pubic bone through a minilaparotomy. Once the pacemaker has been fixed behind the pubic bone, a connecting end or connection portion 18 of wire electrode means 8 is connected to the pacemaker so as to be able to transmit electrical impulses to the nerves in the genital area via the electrodes in contact portion 9.

FIG. 9 once more illustrates the advantages of the implantation method described above, in which contact portion 9 of implanted wire electrode means 8 is placed and fixed in direct proximity to nerves 19 to be stimulated while the guiding of the wire electrode means behind pubic bone 31 and around pubic bone 31 ensures a particularly good prevention of a shift or migration of wire electrode means 8 following implantation. The pacemaker, which is not shown in FIG. 9 and which is preferably also installed behind pubic bone 31, is ideally protected against external trauma by being placed there. Overall, the method described above leads to a very reliable and robust implantation of the neuroprosthesis for stimulating the nerves in the genital area as directly as possible.

FIGS. 10a-10c show an example of an embodiment of an implantation system 20 according to the invention comprising a hollow needle applicator 1 including a tip 4 insertable into and removable from shaft 6 of hollow needle applicator 1, wire electrode means 8, and a pacemaker 21 along with pacemaker fixing means 22. Pacemaker 21 and pacemaker fixing means are optional components of system 20. As is apparent from the two different side vies of pacemaker 21 and wire electrode means 8, at a front end or distal end 23 on which contact portion 9 with electrodes 24 are also disposed, the wire electrode means have a first fixing means 25 with which the end of wire electrode means 8 can be fixed or attached. Preferably, fixing means 25 is used to fix wire electrode means 8 to a cartilage and/or a bone. To this end, non-absorbable suture means (not shown in FIGS. 10a-10c) can be used in addition to fixing means 25. Furthermore, wire electrode means 8 comprises, in a shaft portion 26, a second fixing means 27 which is mobile so as to be movable along wire electrode means 8. Second fixing means 27, too, can be used to additionally fix wire electrode means 8, preferably to the pubic bone. To this end, in the implanted state of wire electrode means 8, mobile second fixing means 27 along wire electrode means 8 can be moved into a position that allows fixation as ideal as possible and protection of wire electrode means 8 against migration.

The illustrations of FIGS. 10a-10c also shows that hollow needle applicator 1 comprise a handle 28 and a measuring device 11 in the area of shaft 6, measuring device 11 being realized in the form of a window 10 provided with a scale 29 or mark, for example. In an alternative embodiment, too, measuring device 11 allows the user to determine how far wire electrode means 8 have been introduced into hollow needle applicator 1. Particularly preferably, the measuring device can be set or individualized so as to be adjustable to a body or patient, preferably based on the records of the preoperative test method.

Figure 11:
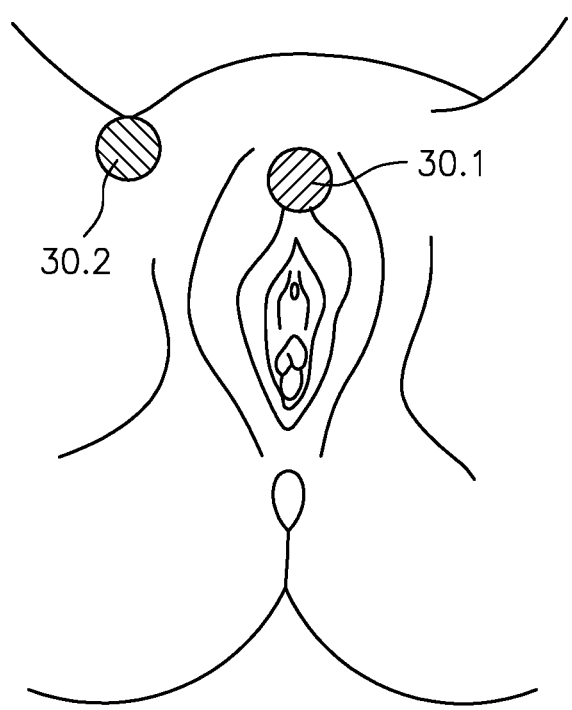
FIG. 11 is a further illustrates implantation methods according to the invention.

FIG. 11 shows a schematic illustration in connection with the performance of the preoperative test method according to the invention. A placement of two removable, preferably adhesive electrodes 30 in genital area 12 of a body 13 is shown. Once electrodes 30 have been placed, a physical condition that exhibits certain symptoms to be treated is induced in the preoperative test method. After or during induction of the physical condition, electrodes 30 are fed or energized with a test current. The test current can preferably have current pulses of 150 to 250 μs in length and preferably with a frequency of 10 to 50 Hz, particularly preferably an amplitude of 5 to 60 mA. A first electrode 30.1 is placed in the area of the clitoris or in the area of the root of the penis, whereas second electrode 30.2 is placed at about the same height, but at a lateral distance of 2 to 3 cm from an outer labium or laterally offset by 2 to 3 cm from the root of the penis. Preferably, the lateral placement of electrode 30.2 can be performed successively on both sides or halves of the body. Likewise, the laterally offset placement of second electrode 30.2 can also be performed at different heights in addition to a placement at about the same height as first electrode 30.1. In both instances, i.e. placement of second electrode 30.2 on different sides or halves of the body and placement of second electrode 30.2 at different heights, the physical condition exhibiting symptoms to be treated is preferably induced or maintained and the electrodes are energized with a test current in order to record or register the changes in the physical symptoms. Instead of a change of the lateral distance between the two electrodes 30.1 and 30.2 and alternatively to a change of the height of second electrode 30.2 relative to first electrode 30.1 a multiple electrode which has multiple individual electrodes that are spatially adjacent and electrically separated from one another and which can be controlled individually can be used to reproduce or replace the lateral variation. Preferably, first electrode 30.1 is energized as a cathode and second electrode 30.2 is energized as an anode. Advantageously, polarity can reverse, in which case the change in the physical symptoms is also recorded as a function of the respective polarity.

The preoperative test method and the record of the change in the physical symptoms form the basis for the later determination regarding a therapeutic outcome to be expected after final implantation of a neuroprosthesis and for optimal performance of an implantation method because the records obtained on the changes in symptoms can also be used to draw conclusions as to an ideal implantation site for the electrodes, in particular for the contact portion of the wire electrode means, and the implantation method can be performed optimally.

REFERENCE SIGNS 1 hollow needle applicator
2 paravulvar incision, first incision
3 finger
4 tip
5 abdominal wall
6 shaft
7 first implantation channel
8 wire electrode means
9 contact portion
10 window
11 measuring device
12 genital area
13 body
14 supravulvar incision, second incision
15 exit area
16 entry area
17 second implantation channel
18 connecting portion
19 nerves
20 implantation system
21 pacemaker
22 pacemaker fixing means
23 front end or distal end
24 electrodes
25 first fixing means
26 shaft portion
27 second fixing means
28 handle
29 scale
30 electrodes
30.1 First electrode
30.2 second electrode
31 pubic bone

The invention claimed is:

1. An implantation method for a wire electrode means (8) into the pelvic area of a human body (13), the implantation method comprising the method steps of:
producing a first temporary implantation channel (7) running from the genital area (12) behind the pubic bone (31) to the abdominal wall (5) for receiving the wire electrode means (8);
introducing the wire electrode means (8) into the first temporary implantation channel (7) from the abdominal wall (5) in such a manner that a contact portion (9) of the wire electrode means (8) protrudes from the human body (13);
producing a second temporary implantation channel (17) which runs under the pubic bone (31) in the genital area (12) and whose exit area (15) from the human body (13) coincides with an entry area (16) of the first temporary implantation channel (7) located in the genital area (12), the contact portion (9) of the wire electrode means (8) thus being introducible into the second temporary implantation channel (17),
transferring the contact portion (9) of the wire electrode means (8) protruding from the human body (13) into the second temporary implantation channel in such a manner that electrodes (24) disposed in the contact portion (9), are placed in an area of the roots of the nerves (19) in the genital area (12).

2. The method according to claim 1, wherein the introducing step is carried out in such a manner that the contact portion (9) protrudes from the first temporary implantation channel (7), in the genital area.

3. The method according to claim 1, wherein the second temporary implantation channel (17) is produced in an area of the pelvic floor.

4. The method according to claim 1, wherein the electrodes (24) are circumferential electrode means.

5. The method according to claim 1, wherein the wire electrode means (8) is anchored to a cartilage and/or bone structure.

6. The method according to claim 5, wherein the cartilage and/or bone structure is the pubic bone (31).

7. The method according to claim 5, wherein the wire electrode means (8) has a fixing means on the contact portion (9), the fixing means allowing the wire electrode means (8) to be fixed to the cartilage and/or bone structure.

8. The method according to claim 5, wherein the wire electrode means (8) has a mobile fixing means in a shaft portion, the mobile fixing means allowing the wire electrode means (8) to be fixed to the cartilage and/or bone structure.

9. The method according to claim 1, wherein the first and/or the second temporary implantation channel (17) is/are produced using a curved hollow needle applicator (1) which comprises a hollow needle channel enclosed by a shaft (6) and forming the respective first and/or second temporary implantation channel.

10. The method according to claim 9, wherein, in the first and/or the second temporary implantation channel (17), a tip (4) is disposed on and can be removed from the hollow needle applicator (1) at a front end, and wherein the tip (4) blocks access to the hollow needle channel and fills part of the hollow needle channel.

11. The method according to claim 10, wherein the tip (4) is extracorporeally removed from the hollow needle applicator (1) at the front end after production of the first and/or second temporary implantation channel.

12. The method according to claim 9, wherein in the production of the first temporary implantation channel (7), the curved hollow needle applicator (1) is introduced while being in contact with a lower edge of the pubic ramus until it penetrates the urogenital diaphragm, the retropubic space and the abdominal wall (5), exit from the abdominal wall (5) being performed in such a manner that exit occurs above the pubic bone (31) and a shaft (6) of the hollow needle applicator (1) surrounding the hollow needle channel is in contact with the pubic bone (31).

13. The method according to claim 9, the wire electrode means (8) is introduced into the hollow needle channel, and then the hollow needle applicator (1) is removed from the human body (13) by being retracted.

14. The method according to claim 13, wherein the hollow needle applicator (1) is retracted in a direction of a puncture or in a direction of an entry point.

15. The method according to claim 1, wherein producing the first temporary implantation channel (7) comprises making an incision, the incision being made in the genital area (12) of the human body (13), 0.5 cm to 1.5 cm below the external urethral meatus or 0.5 cm to 1.5 cm below the infrapubic parapenile.

16. The method according to claim 15, wherein producing the second temporary implantation channel (17) comprises making a second incision, the second incision, on a median axis of the human body, being made below the caudal border of the inferior pubic ramus, just above the root of the penis or the clitoral glands and laterally offset therefrom by 3 mm to 5 mm.

17. The method according to claim 1, wherein a connecting end of the wire electrode means (8) that faces away from the contact portion (9) is connected to a pacemaker (21) which is placed behind the pubic bone (31), opposite the contact portion (9) of the wire electrode means (8).

18. The method according to claim 1, wherein the surgical method steps are performed under general anesthesia, spinal anesthesia or epidural anesthesia.

* * * * *